United States Patent
Arruda et al.

(10) Patent No.: US 11,708,570 B2
(45) Date of Patent: Jul. 25, 2023

(54) COMPOSITIONS AND METHODS FOR MODULATING FACTOR IX FUNCTION

(71) Applicant: The Children's Hospital of Philadelphia, Philadelphia, PA (US)

(72) Inventors: Valder R. Arruda, Philadelphia, PA (US); Rodney M. Camire, Sicklerville, NJ (US); Benjamin Samelson-Jones, Wynnewood, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 220 days.

(21) Appl. No.: 16/320,137

(22) PCT Filed: Jul. 27, 2017

(86) PCT No.: PCT/US2017/044104
§ 371 (c)(1),
(2) Date: Jan. 24, 2019

(87) PCT Pub. No.: WO2018/022844
PCT Pub. Date: Feb. 1, 2018

(65) Prior Publication Data
US 2020/0248161 A1 Aug. 6, 2020

Related U.S. Application Data

(60) Provisional application No. 62/367,321, filed on Jul. 27, 2016.

(51) Int. Cl.
| | | |
|---|---|---|
| *C12N 9/64* | (2006.01) | |
| *A61K 38/36* | (2006.01) | |
| *A61P 7/04* | (2006.01) | |
| *C12N 15/86* | (2006.01) | |
| *A61K 38/00* | (2006.01) | |

(52) U.S. Cl.
CPC ............. *C12N 9/644* (2013.01); *A61P 7/04* (2018.01); *C12N 15/86* (2013.01); *A61K 38/00* (2013.01); *C12Y 304/21022* (2013.01)

(58) Field of Classification Search
None
See application file for complete search history.

(56) References Cited

U.S. PATENT DOCUMENTS

| | | |
|---|---|---|
| 2008/0102115 A1 | 5/2008 | Oyhenart et al. |
| 2013/0157281 A1 | 6/2013 | Beyer et al. |
| 2013/0243855 A1 | 9/2013 | Oyhenart et al. |
| 2016/0201047 A1 | 7/2016 | Madison et al. |

FOREIGN PATENT DOCUMENTS

| | | |
|---|---|---|
| WO | 2007/059513 A2 | 5/2007 |
| WO | 2007/135182 A2 | 11/2007 |
| WO | 2011/014890 A1 | 2/2011 |
| WO | 2013/049804 A1 | 4/2013 |
| WO | 2016/028872 A2 | 2/2016 |

OTHER PUBLICATIONS

Hartmann, et al., "Factor IX mutants with enhanced catalytic activity" J. Thromb. Haemost. (2009) 7(10):1656-62.
George, et al. "Hemophilia B Gene Therapy with a High-Specific-Activity Factor IX Variant" N. Engl. J. Med. (2017) 377(23):2215-2227.
Simioni, et al., "X-linked thrombophilia with a mutant factor IX (factor IX Padua)" N. Engl. J. Med. (2009) 361(17):1671-5.
Quade-Lyssy, et al., "Oral gene therapy for hemophilia B using chitosan-formulated FIX mutants" J. Thromb. Haemost. (2014) 12(6):932-42.
Cheung, et al., "The binding of human factor IX to endothelial cells is mediated by residues 3-11" J. Biol. Chem. (1992) 267(29):20529-31.
Lin, et al., "Generation of a novel factor IX with augmented clotting activities in vitro and in vivo" J. Thromb. Haemost. (2010) 8(8):1773-83.
Sichler, et al., "Physiological fIXa activation involves a cooperative conformational rearrangement of the 99-loop" J. Biol. Chem. (2003) 278(6):4121-6.
Milanov, et al., "Engineered factor IX variants bypass FVIII and correct hemophilia A phenotype in mice" Blood (2012) 119(2):602-11.
Misenheimer, et al., "The heparin-binding exosite is critical to allosteric activation of factor IXa in the intrinsic tenase complex: the role of arginine 165 and factor X" Biochemistry (2007) 46(26):7886-95.
Perot, et al., "Expression and characterization of a novel human recombinant factor IX molecule with enhanced in vitro and in vivo clotting activity" Thromb. Res. (2015) 135(5):1017-24.
Kao, et al., "Incorporation of the factor IX Padua mutation into FIX-Triple improves clotting activity in vitro and in vivo" Thromb. Haemost. (2013) 110(2):244-56.
Finn, et al., "The efficacy and the risk of immunogenicity of FIX Padua (R338L) in hemophilia B dogs treated by AAV muscle gene therapy" Blood (2012) 120(23):4521-3.
Monahan, et al., "Employing a gain-of-function factor IX variant R338L to advance the efficacy and safety of hemophilia B human gene therapy: preclinical evaluation supporting an ongoing adeno-associated virus clinical trial" Hum. Gene Ther. (2015) 26(2):69-81.

*Primary Examiner* — Marsha Tsay
(74) *Attorney, Agent, or Firm* — Robert C. Netter, Jr.; Dann, Dorfman, Herrell & Skillman (57) ABSTRACT

Factor IX/IXa variants and methods of use thereof are disclosed.

9 Claims, 5 Drawing Sheets
Specification includes a Sequence Listing.

```
  1 MQRVNMIMAE SPGLITICLL GYLLSAECTV FLDHENANKI LNRPKRYNSG KLEEFVQGNL
 61 ERECMEEKCS FEEAREVFEN TERTTEFWKQ YVDGDQCESN PCLNGGSCKD DINSYECWCP
121 FGFEGKNCEL DVTCNIKNGR CEQFCKNSAD NKVVCSCTEG YRLAENQKSC EPAVPFPCGR
181 VSVSQTSKLT RAETVFPDVD YVNSTEAETI LDNITQSTQS FNDFTRVVGG EDAKPGQFPW
241 QVVLNGKVDA FCGGSIVNEK WIVTAAHCVE TGVKITVVAG EHNIEETEHT EQKRNVIRII
301 PHHNYNAAIN KYNHDIALLE LDEPLVLNSY VTPICIADKE YTNIFLKFGS GYVSGWGRVF
361 HKGRSALVLQ YLRVPLVDRA TCLRSTKFTI YNNMFCAGFH EGGRDSCQGD SGGPHVTEVE
421 GTSFLTGIIS WGEECAMKGK YGIYTKVSRY VNWIKEKTKL T
```

Figure 1A

```
YNSG KLEEFVQGNLERECMEEKCS FEEAREVFEN TERTTEFWKQ YVDGDQCESN
PCLNGGSCKD DINSYECWCPFGFEGKNCEL DVTCNIKNGR CEQFCKNSAD
NKVVCSCTEG YRLAENQKSC EPAVPFPCGRVSVSQTSKLT R
```

<u>Light Chain</u>

```
AETVFPDVD YVNSTEAETI LDNITQSTQS FNDFTRVVGG EDAKPGQFPW
QVVLNGKVDA FCGGSIVNEK WIVTAAHCVE TGVKITVVAG EHNIEETEHT
EQKRNVIRII PHHNYNAAIN KYNHDIALLE LDEPLVLNSY VTPICIADKE
YTNIFLKFGS GYVSGWGRVF HKGRSALVLQ YLRVPLVDRA TCLRSTKFTI
YNNMFCAGFH EGGRDSCQGD SGGPHVTEVE GTSFLTGIIS WGEECAMKGK
YGIYTKVSRY VNWIKEKTKL T
```

<u>Heavy Chain</u>

Figure 1B

```
YNSG KLEEFVQGNLERECMEEKCS FEEAREVFEN TERTTEFWKQ YVDGDQCESN
PCLNGGSCKD DINSYECWCPFGFEGKNCEL DVTCNIKNGR CEQFCKNSAD
NKVVCSCTEG YRLAENQKSC EPAVPFPCGRVSVSQTSKLT R
```

<u>Light Chain</u>

```
VVGG EDAKPGQFPW QVVLNGKVDA FCGGSIVNEK WIVTAAHCVE TGVKITVVAG
EHNIEETEHT EQKRNVIRII PHHNYNAAIN KYNHDIALLE LDEPLVLNSY
VTPICIADKE YTNIFLKFGS GYVSGWGRVF HKGRSALVLQ YLRVPLVDRA
TCLRSTKFTI YNNMFCAGFH EGGRDSCQGD SGGPHVTEVE GTSFLTGIIS
WGEECAMKGK YGIYTKVSRY VNWIKEKTKL T
```

<u>Heavy Chain</u>

Figure 1C

```
a tgcagcgcgtgaacatgatcatggcagaat
caccaggcctcatcaccatctgccttttaggatatctactcagtgctgaatgtacagttt
ttcttgatcatgaaaacgccaacaaaattctgaatcggccaaagaggtataattcaggta
aattggaagagtttgttcagggaaccttgagagagaatgtatggaagaaaagtgtagtt
ttgaagaagcacgagaagtttttgaaaacactgaaagaacaactgaattttggaagcagt
atgttgatggagatcagtgtgagtccaatccatgtttaaatggcggcagttgcaaggatg
acattaattcctatgaatgttggtgtccctttggatttgaaggaaagaactgtgaattag
atgtaacatgtaacattaagaatggcagatgcgagcagttttgtaaaaatagtgctgata
acaaggtggtttgctcctgtactgagggatatcgacttgcagaaaaccagaagtcctgtg
aaccagcagtgccatttccatgtggaagagtttctgtttcacaaacttctaagctcaccc
gtgctgagactgttttcctgatgtggactatgtaaattctactgaagctgaaaccattt
tggataacatcactcaaagcacccaatcatttaatgacttcactcgggttgttggtggag
aagatgccaaaccaggtcaattcccttggcaggttgttttgaatggtaaagttgatgcat
tctgtggaggctctatcgttaatgaaaaatggattgtaactgctgcccactgtgttgaaa
ctggtgttaaaattacagttgtcgcaggtgaacataatattgaggagacagaacatacag
agcaaaagcgaaatgtgattcgaattattcctccaccaactacaatgcagctattaata
agtacaaccatgacattgcccttctggaactggacgaaccctagtgctaaacagctacg
ttacacctatttgcattgctgacaaggaatacacgaacatcttcctcaaatttggatctg
gctatgtaagtggctggggaagagtcttccacaaagggagatcagctttagttcttcagt
accttagagttccacttgttgaccgagccacatgtcttcgatctacaaagttcaccatct
ataacaacatgttctgtgctggcttccatgaaggaggtagagattcatgtcaaggagata
gtggggacccccatgttactgaagtggaagggaccagtttcttaactggaattattagct
ggggtgaagagtgtgcaatgaaaggcaaatatggaatatataccaaggtatcccggtatg
tcaactggattaaggaaaaaacaaagctcacttaa
```

COMPOSITIONS AND METHODS FOR MODULATING FACTOR IX FUNCTION

This application is a §371 application of PCT/US2017/044104, filed Jul. 27, 2017, which claims priority under 35 U.S.C. §119(e) to U.S. Provisional Patent Application No. 62/367,321, filed Jul. 27, 2016. The foregoing applications are is incorporated by reference herein.

FIELD OF THE INVENTION

The present invention relates to the fields of medicine and hematology. More specifically, the invention provides novel Factor IX variants and methods of using the same to modulate the coagulation cascade in patients in need thereof.

BACKGROUND OF THE INVENTION

Several publications and patent documents are cited throughout the specification in order to describe the state of the art to which this invention pertains. Each of these citations is incorporated herein by reference as though set forth in full.

In response to vascular injury such as a cut, coagulation enzymes are activated in a stepwise manner, ultimately resulting in the formation of a blood clot at the site of injury. Thrombin is generated from its inactive precursor prothrombin in the final step of this cascade and subsequently produces the fibrous clot. Activated Factor IX (FIXa) is a key component of this system as it is the serine protease of the intrinsic Xase complex, which also comprises the cofactor activated Factor VIII (FVIIIa). This enzyme, assembled on cells with exposed anionic membranes, rapidly converts Factor X to activated Factor X (FXa). FXa and its co-factor, activated Factor V (FVa), form prothrombinase, the enzyme complex that activates thrombin.

The importance of Factor IX is reflected by the occurrence of the bleeding disorder hemophilia B in individuals carrying mutations in the Factor IX gene. In bleeding disorders such as hemophilia B, a defect or deficiency of Factor IX results in inadequate FXa generation and, therefore, inadequate thrombin formation. Replacement of the missing protein is the mainstay of hemophilia treatment. Although effective, there are several limitations with current protein replacement therapies. For example, current therapies suffer from the short-half life of the proteins administered, thereby requiring multiple intravenous injections at high doses. Therefore, there is an obvious need for clotting factors with improved biological properties.

SUMMARY OF THE INVENTION

In accordance with the present invention, compositions and methods for the modulation of hemostasis in patients in need thereof are provided. More specifically, Factor IX/Factor IXa variants which modulate (e.g., increase) hemostasis are provided. In a particular embodiment, the variant comprises at least one substitution of the Glu at position 410; the Val at position 223; the Phe at position 342; the Thr at position 343; and/or the Asn at position 406. In a particular embodiment, the variant comprises at least one substitution of the Glu at position 410; the Val at position 223; and/or the Asn at position 406. In a particular embodiment, the Factor IX/Factor IXa variant further comprises a substitution of the Arg at position 338, particularly a substitution of the Arg at position 338 with a Leu. Nucleic acids encoding the variants of the invention are also disclosed as are methods of use thereof. Such nucleic acid molecules may optionally encode an intracellular cleavage site (e.g., PACE/furin). Another aspect of the invention includes host cells expressing the variant of the invention. Methods for isolating and purifying the variants are also disclosed.

Pharmaceutical compositions comprising the variants of the invention in a carrier are also provided. The invention also includes methods for the treatment of a hemostasis related disorder in a patient in need thereof comprising administration of a therapeutically effective amount of the variant or a nucleic acid molecule encoding the variant to the subject. Such methods have efficacy in the treatment of disorders where a pro-coagulant is needed (e.g., to reduce or inhibit bleeding) and include, without limitation, hemophilia, particularly hemophilia B.

DETAILED DESCRIPTION OF THE INVENTION

Herein, novel Factor IX variants (zymogens) are provided. In particular, Factor IX variants comprising a mutation of the Glu at position 410, the Val at position 223, the Phe at position 342, the Thr at position 343, and/or the Asn at position 406 are provided.

In a particular embodiment, the Factor IX variant comprises at least one substitution of the Glu at position 410; the Val at position 223; and/or the Asn at position 406. The Factor IX variants may further comprise a mutation of the Arg at position 338 (e.g., R338L). The Factor IX variants of the instant invention have greater specific activity compared to wild-type Factor IX.

The blood coagulation response is a defense mechanism that has evolved to protect organisms from significant loss of blood following injury. As explained briefly hereinabove, coagulation proceeds through a series of proteolytic reactions, each of which converts an inert zymogen (inactive) in blood to a serine protease (active) product. Thrombin, the final serine protease product of the blood coagulation cascade, activates platelets and cleaves a structural protein (fibrinogen) to generate fibrin, thereby providing a meshwork which physically prevents blood from leaving the vessel. Deviation from this process leads to the pathological state of bleeding. This is particularly true in the case of a defect or deficiency of Factor IX. Such a deficiency in Factor IX activity results in the inherited bleeding disorder hemophilia B. Protein replacement therapy with intravenously delivered plasma-derived or recombinant Factor IX is the standard of care for hemophilia B patients. While this therapy is effective, this therapy requires frequent (e.g., 2-3 times per week) intravenous administration of large amounts of Factor IX. The present invention provides Factor IX variants which have increased activity compared to wild-type FIX, thereby allowing for a quicker response (e.g., for administration to treat a bleeding episode) and/or decrease in the amount of protein needed to be administered (e.g., reduction in the dosage requirements for protein replacement therapy).

Factor IX circulates in plasma as an inactive zymogen (57 kDa) at a concentration of approximately 90 nM. Factor IX is initially synthesized in the liver harboring a ~40 amino acid pre-pro-leader sequence which is removed upon secretion of the protein. Upon vascular damage, Factor IX is activated to FIXa following cleavage of two bonds by either the Factor VIIa/tissue factor (TF) complex or Factor XIa— releasing a 35-residue activation peptide. Activation of Factor IX follows a well-described mechanism. Bond cleavage at a highly conserved site ($R^{15}$ -$V^{16}$VGG, in chymotrypsin numbering system) unmasks a new N-terminus ($V^{16}V^{17}$GG) of the heavy chain. After cleavage, the intermediate is in a "zymogen-like state," which rapidly equilibrates to the protease state after the newly generated N-terminus inserts into the activation pocket and forms a salt-bridge with the $Asp^{194}$. This interaction is a defining characteristic of the conversion of zymogen to active enzyme. The zymogen state and the protease state exist in an equilibrium that can be shifted depending on various ligands or cofactors. Free FIXa is rapidly eliminated by reactions with circulating serpins, most notably antithrombin III (ATIII).

The instant invention encompasses variant Factor IX molecules including FIXa variants, Factor IX variants, Factor IX prepropeptide variants, and Factor IX propeptide variants. For simplicity, the variants are generally described throughout the application in the context of FIX. However, the invention contemplates and encompasses Factor IXa, Factor IX prepropeptide, and Factor IX propeptide molecules having the same amino acid substitutions.

Figure 1A:
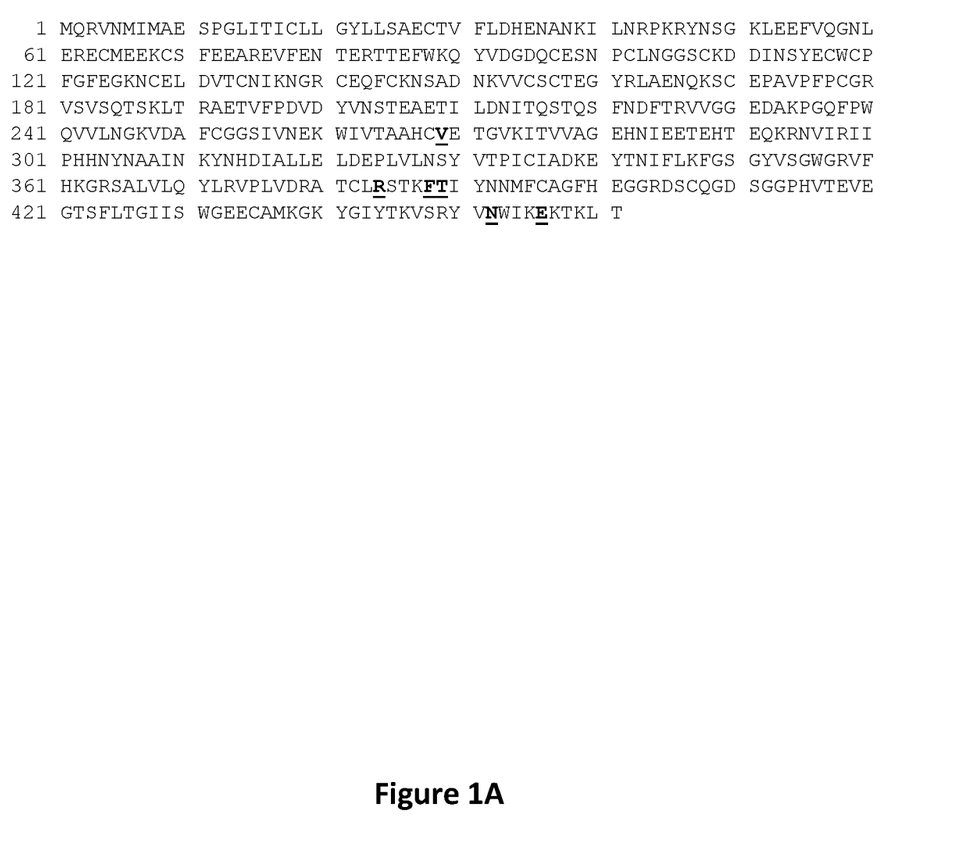
FIG. 1A provides an amino acid sequence of human Pre-Pro-Factor IX (SEQ ID NO: 1). The underlined and bolded residues are positions 223, 338, 342, 343, 406, and 410, based on Factor IX numbering (see FIG. 1B).
Figure 1B:
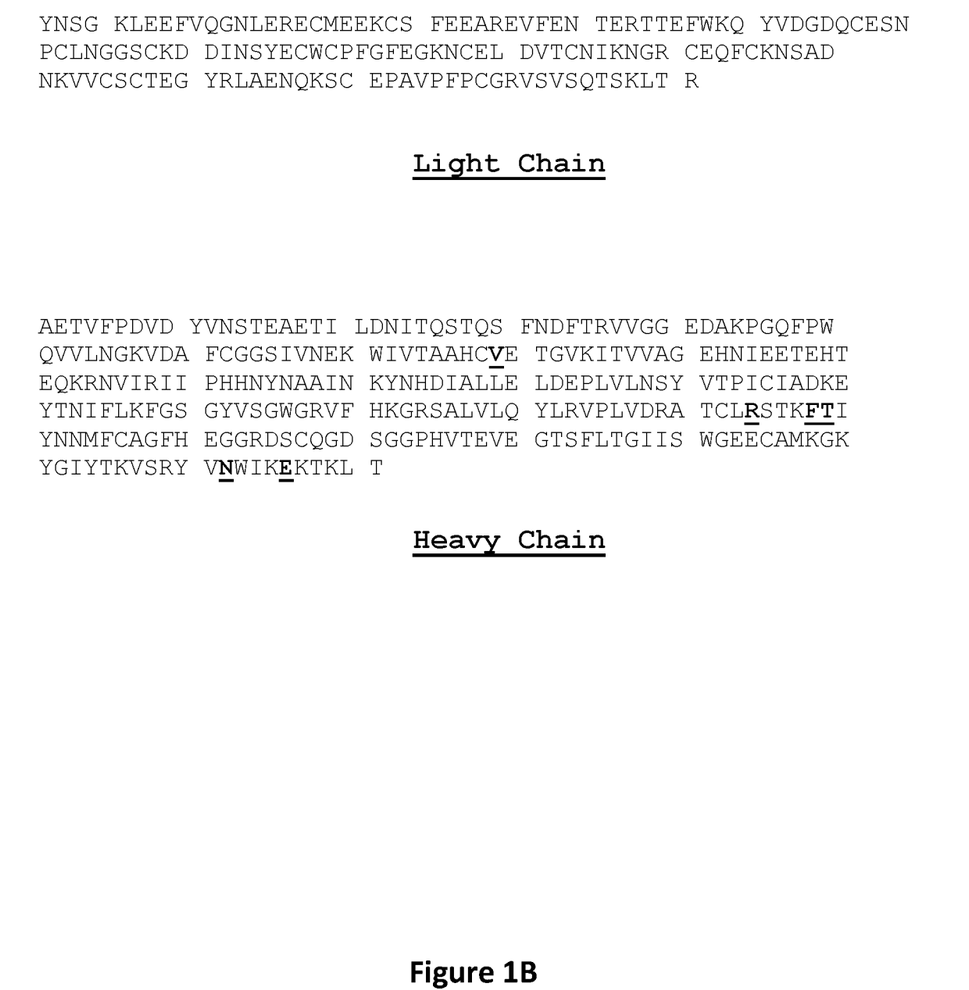
FIG. 1B provides an amino acid sequence of the light chain (SEQ ID NO: 2) and heavy chain (SEQ ID NO: 3) of Factor IX.
Figure 1C:
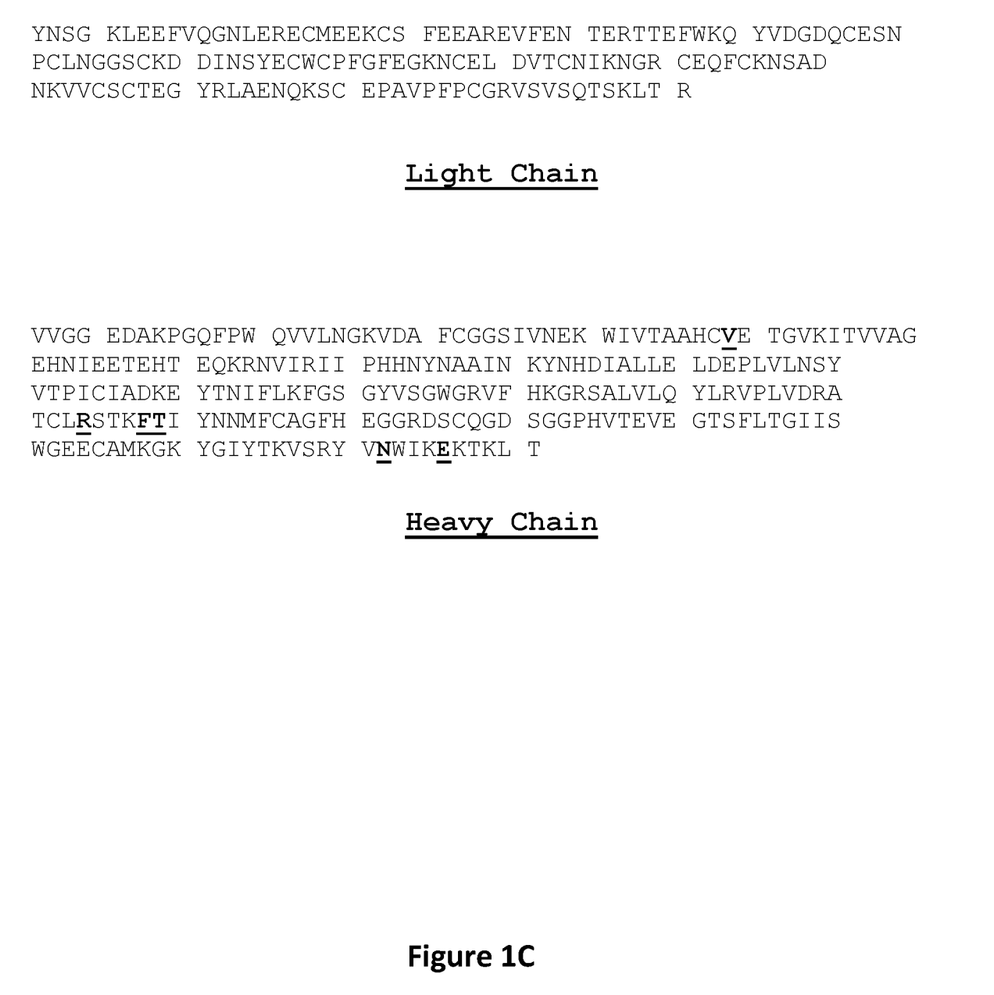
FIG. 1C provides an amino acid sequence of the light chain (SEQ ID NO: 2) and heavy chain (SEQ ID NO: 4) of activated Factor IX (FIXa).
Figure 1D:
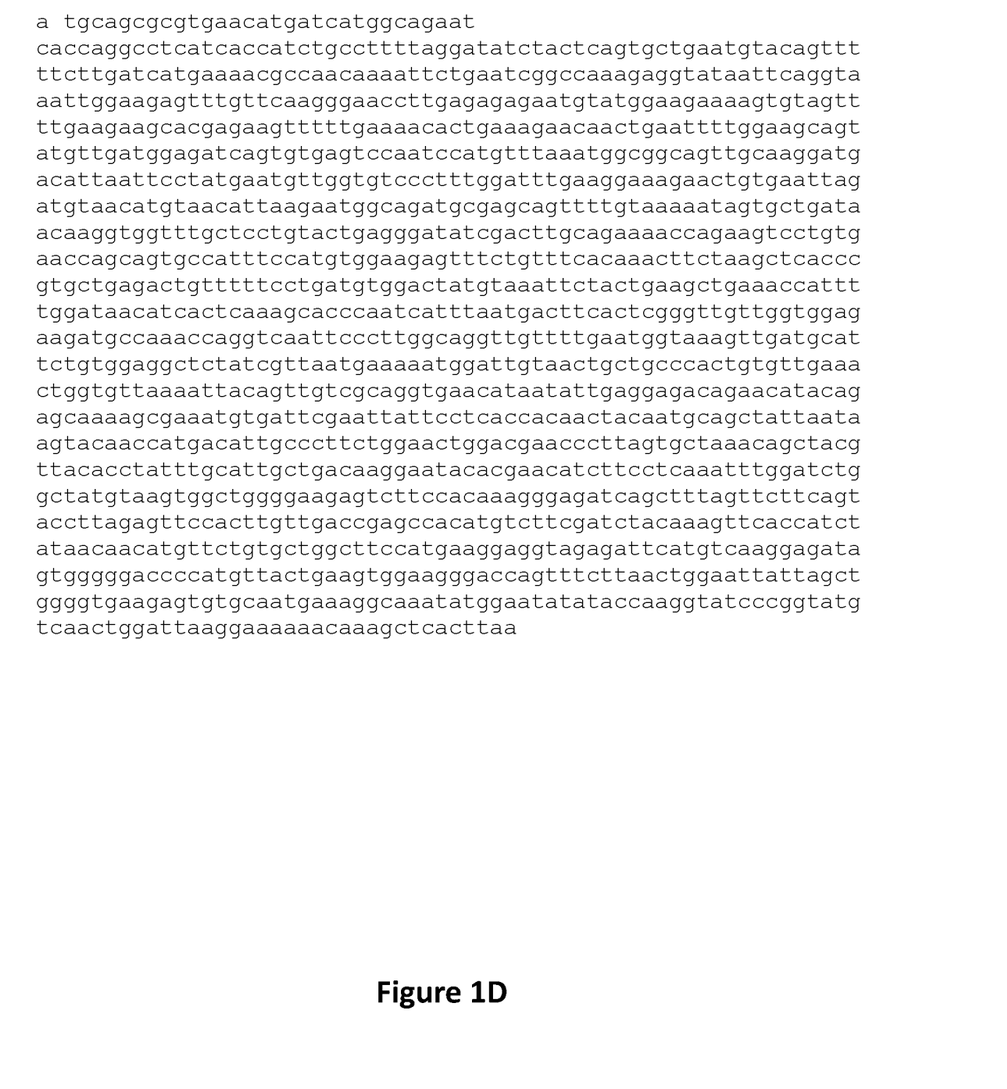
FIG. 1D provides a nucleic acid sequence (SEQ ID NO: 5) which encodes human Factor IX preproprotein.

The FIX variants of the instant invention can be from any mammalian species. In a particular embodiment, the FIX variant is human. Gene ID: 2158 and GenBank Accession Nos. NM_000133.3 and NP-000124.1 provide examples of the amino acid and nucleotide sequences of wild-type human Factor IX preproprotein. FIG. 1A provides SEQ ID NO: 1, which is an example of the amino acid sequence of the human Factor IX preproprotein. The Factor IX prepropetide comprises a signal peptide from amino acids 1-28 and a propeptide sequence from amino acids 29-46. The cleavage of the propeptide yields a protein with a new terminus sequence of Tyr-Asn-Ser. Factor IX is also cleaved by the FVIIa/TF complex or FXIa into a mature two-chain form (light and heavy) at an arginyl-alanine peptide bond to generate the Factor IX zymogen. The two chains are linked via a disulfide bond. FIG. 1B provides SEQ ID NOs: 2 and 3, which are examples of the amino acid sequence of the human Factor IX light and heavy chains, respectively. Factor IX is activated by the cleavage of the 35 amino acid activation peptide at an arginyl-valine peptide bond by the FVIIa/TF complex or FXIa to yield a new amino-terminal sequence of VVGG (SEQ ID NO: 6) for wild-type FIXa heavy chain (SEQ ID NO: 4). FIG. 1C provides SEQ ID NOs: 2 and 4, which are examples of the amino acid sequence of the human FIXa light and heavy chains. Notably, the above proteolytic cleavage events may be imprecise, thereby leading to addition or loss of amino acids (e.g., 1, 2, 3, or more amino acids) at the cleavage sites. FIG. 1D provides a nucleic acid sequence (SEQ ID NO: 5) which encodes human Factor IX preproprotein. Nucleic acid molecules which encode Factor IX and FIXa can be readily determined from the provided amino acid and nucleotide sequences.

In a particular embodiment, the variant of the instant invention has at least 75%, 80%, 85%, 90%, 95%, 97%, 99%, or 100% identity with SEQ ID NO: 1, particularly at least 90%, 95%, 97%, or 99% identity. In a particular embodiment, the variant of the instant invention has at least 75%, 80%, 85%, 90%, 95%, 97%, 99%, or 100% identity with amino acids 29-461 of SEQ ID NO: 1, particularly at least 90%, 95%, 97%, or 99% identity. In a particular embodiment, the variant of the instant invention has at least 75%, 80%, 85%, 90%, 95%, 97%, 99%, or 100% identity with amino acids 47-461 of SEQ ID NO: 1, particularly at least 90%, 95%, 97%, or 99% identity. In a particular embodiment, the variant comprises a light and heavy chain, wherein the light chain has at least 75%, 80%, 85%, 90%, 95%, 97%, 99%, or 100% identity with SEQ ID NO: 2, particularly at least 90%, 95%, 97%, or 99% identity, and wherein the heavy chain has at least 75%, 80%, 85%, 90%, 95%, 97%, 99%, or 100% identity with SEQ ID NO: 3, particularly at least 90%, 95%, 97%, or 99% identity. In a particular embodiment, the variant comprises a light and heavy chain, wherein the light chain has at least 75%, 80%, 85%, 90%, 95%, 97%, 99%, or 100% identity with SEQ ID NO: 2, particularly at least 90%, 95%, 97%, or 99% identity, and wherein the heavy chain has at least 75%, 80%, 85%, 90%, 95%, 97%, 99%, or 100% identity with SEQ ID NO: 4, particularly at least 90%, 95%, 97%, or 99% identity. The identity percentages above exclude the substitutions of the instant invention (e.g., those at positions 223, 338, 342, 343, 406, and/or 410).

The variants of the instant invention may also be post-translationally modified (γ-carboxylation). The variants may be post-translationally modified in a cell or in vitro. The variants of the instant invention may also be pegylated or glycopegylated (see, e.g., nonacog beta pegol; Collins et al. (2014) Blood 124: 3880-3886). For example, polyethylene glycol (PEG) (e.g., 40 kDa PEG) may be attached to the variant (e.g., within the activation peptide). In a particular embodiment, the variants of the instant invention may be fused to albumin (see, e.g., Santagostino et al. (2016) Blood 127: 1761-1769; Metzner et al. (2009) Thromb, Haemost., 102: 634-44; Nolte et al. (2012) J. Thromb. Haemost., 10: 1591-9; Herzog et al. (2014) Thromb. Res., 133: 900-7; Schulte (2009) Thromb. Res., 124: S6-S8). For example, the variant may be linked to the albumin via a cleavable linker (e.g., a linker based on the activation peptide). In a particular embodiment, the variant of the instant invention is linked to an Fc region (e.g., Fc domain of $IgG_1$; dimer or monomer) (see e.g., eftrenonacog alfa (Alprolix®); Powell et al. (2013) N. Engl. J. Med., 369: 2313-2323; Peters et al. (2010) Blood 115: 2057-64; Shapiro et al. (2012) Blood 119: 666-72). For example, the variant may be linked to the Fc domain (e.g., hinge and $CH_2$ and $CH_3$ domains (e.g., from $IgG_1$)) via a linker (cleavable or uncleavable).

The FIX variants of the instant invention may comprise at least one substitution at position 223, 342, 343, 406, and/or 410. In a particular embodiment, the FIX variants of the instant invention may comprise at least one substitution at position 223, 406, and/or 410.

In a particular embodiment, the glutamic acid at position 410 is substituted with a non-acidic amino acid (e.g., not Asp). In a particular embodiment, the glutamic acid at position 410 is substituted with a basic amino acid (e.g., Arg, His, or Lys) or a polar amino acid (e.g., Ser, Thr, or Tyr). In a particular embodiment, the glutamic acid at position 410 is substituted with lysine, tyrosine, arginine, or histidine. In a particular embodiment, the glutamic acid at position 410 is substituted with lysine or tyrosine. In a particular embodiment, the glutamic acid at position 410 is substituted with lysine.

In a particular embodiment, the asparagine at position 406 is substituted with a basic amino acid (e.g., Arg, His, or Lys). In a particular embodiment, the asparagine at position 406 is substituted with arginine, lysine, or glutamine. In a particular embodiment, the asparagine at position 406 is substituted with arginine or lysine. In a particular embodiment, the asparagine at position 406 is substituted with arginine.

In a particular embodiment, the valine at position 223 is substituted with a basic amino acid (e.g., Arg, His, or Lys), acidic amino acid (e.g., Asp or Glu), or a polar amino acid (e.g., Ser, Thr, Tyr, Asn, or Gln). In a particular embodiment, the valine at position 223 is substituted with a polar amino acid. In a particular embodiment, the valine at position 223 is substituted with tyrosine.

In a particular embodiment, the phenylalanine at position 342 is substituted with a basic amino acid (e.g., Arg, His, or Lys), acidic amino acid (e.g., Asp or Glu), or a polar amino acid (e.g., Ser, Thr, Tyr, Asn, or Gln). In a particular embodiment, the phenylalanine at position 342 is substituted with a basic amino acid. In a particular embodiment, the phenylalanine at position 342 is substituted with histidine.

In a particular embodiment, the threonine at position 343 is substituted with a basic amino acid (e.g., Arg, His, or Lys), acidic amino acid (e.g., Asp or Glu), a hydrophobic amino acid (e.g., Ala, Ile, Leu, Met, Phe, Val, Pro, or Gly) or a polar amino acid (e.g., Ser, Thr, Tyr, Asn, or Gln). In a particular embodiment, the threonine at position 343 is substituted with a basic amino acid. In a particular embodiment, the threonine at position 343 is substituted with methionine, lysine, arginine, glutamine, or glycine. In a particular embodiment, the threonine at position 343 is substituted with methionine, lysine, arginine, or glutamine. In a particular embodiment, the threonine at position 343 is substituted with methionine, lysine, or arginine. In a particular embodiment, the threonine at position 343 is substituted with methionine or lysine. In a particular embodiment, the threonine at position 343 is substituted with methionine.

The variants of the instant invention may comprise at least one of the above substitutions at position 223, 342, 343, 406, and/or 410. The variants of the instant invention may further comprise at least one other substitution. In a particular embodiment, the variant further comprises a substitution of the arginine at position 338. In a particular embodiment, the arginine at position 338 is substituted with a non-basic amino acid (e.g., not His, or Lys). In a particular embodiment, the arginine at position 338 is substituted with a nonpolar amino acid (e.g., Gly, Ala, Leu, Val, Ile, or Met). In a particular embodiment, the arginine at position 338 is substituted with leucine.

Nucleic acid molecules encoding the above variants are also encompassed by the instant invention. Nucleic acid molecules encoding the variants may be prepared by any method known in the art. The nucleic acid molecules may be maintained in any convenient vector, particularly an expression vector.

Compositions comprising at least one variant polypeptide and at least one carrier are also encompassed by the instant invention. Compositions comprising at least one variant nucleic acid molecule and at least one carrier are also encompassed by the instant invention. Except insofar as any conventional carrier is incompatible with the variant to be administered, its use in the pharmaceutical composition is contemplated. In a particular embodiment, the carrier is a pharmaceutically acceptable carrier for intravenous administration.

Definitions

Various terms relating to the biological molecules of the present invention are used hereinabove and also throughout the specification and claims.

The phrase "hemostasis related disorder" refers to bleeding disorders such as, without limitation, hemophilia A, hemophilia B, hemophilia A and B patients with inhibitory antibodies, deficiencies in at least one coagulation factor (e.g., Factors VII, IX, X, XI, V, XII, II, and/or von Willebrand factor; particularly Factor IX), combined FV/FVIII deficiency, vitamin K epoxide reductase C1 deficiency, gamma-carboxylase deficiency; bleeding associated with trauma, injury, thrombosis, thrombocytopenia, stroke, coagulopathy (hypocoagulability), disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency. In a particular embodiment, the hemostasis related disorder is hemophilia B.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote. With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

With respect to protein, the term "isolated protein" is sometimes used herein. This term may refer to a protein produced by expression of an isolated nucleic acid molecule of the invention. Alternatively, this term may refer to a protein which has been sufficiently separated from other proteins with which it would naturally be associated (e.g., so as to exist in "substantially pure" form).

The term "vector" refers to a carrier nucleic acid molecule (e.g., RNA or DNA) into which a nucleic acid sequence can be inserted, e.g., for introduction into a host cell where it may be expressed and/or replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "substantially pure" refers to a preparation comprising at least 50-60% by weight the compound of interest (e.g., nucleic acid, oligonucleotide, protein, etc.), particularly at least 75% by weight, or at least 90-99% or more by weight of the compound of interest. Purity may be measured by methods appropriate for the compound of interest (e.g. chromatographic methods, agarose or polyacrylamide gel electrophoresis, HPLC analysis, and the like).

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

Preparation of Variant Encoding Nucleic Acid Molecules and Polypeptides

Nucleic acid molecules encoding the variants of the invention may be prepared by using recombinant DNA technology methods. The availability of nucleotide sequence information enables preparation of isolated nucleic acid molecules of the invention by a variety of means. For example, nucleic acid sequences encoding a variant may be isolated from appropriate biological sources using standard protocols well known in the art.

Nucleic acids of the present invention may be maintained as RNA or DNA in any convenient cloning vector. In a particular embodiment, clones are maintained in a plasmid cloning/expression vector, which is propagated in a suitable E. coli host cell. Alternatively, the nucleic acids may be maintained in a vector suitable for expression in mammalian cells (e.g., T cells, hematopoietic cells, etc.). In cases where post-translational modification affects variant function, it is preferable to express the molecule in mammalian cells.

In one embodiment, the nucleic acids encoding the variants of the instant invention may be further modified via insertion of an intracellular proteolytic cleavage site (the instant invention also encompasses the resultant polypeptide both before and after cleavage). In order to express FIXa variants in mammalian cells, an intracellular proteolytic cleavage site (e.g., PACE/furin cleavage site) can be inserted between positions $Arg^{15}$ and $Val^{16}$ in the variant Factor IX. Such cleavage sites include, without limitation: Arg-Xaa-(Arg/Lys)-Arg (SEQ ID NO: 7), Arg-Lys-Arg, or Arg-Lys-Arg-Arg-Lys-Arg (SEQ ID NO: 8). These cleavage sites are efficiently recognized by proteases (PACE/furin-like enzymes) within the cell and are removed. This results in a processed variant FIXa in which the heavy chain on the molecule begins at position 16. Introduction of this cleavage site at this position will allow for the intracellular conversion of Factor IX to FIXa. In another embodiment, part or all of the 35 amino acid activation peptide can be removed and the intracellular protease cleavage site can be introduced in its place which will result in FIXa variants upon expression. Ultimately these types of modifications allow for secretion of the "active" processed form of variant Factor IX from a cell that expresses the modified variant Factor IX. Secretion of the cleaved factor obviates a need for proteolytic cleavage during blood clotting or following the isolation of the protein.

Variant encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting variant expression.

The variants of the present invention may be prepared in a variety of ways, according to known methods. The protein may be purified from appropriate sources (e.g., transformed bacterial or animal cultured cells or tissues which express variants), for example, by immunoaffinity purification. The availability of nucleic acid molecules encoding the variants enables production of the variants using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available.

Alternatively, larger quantities of variant may be produced by expression in a suitable prokaryotic or eukaryotic expression system. For example, part or all of a DNA molecule encoding the variant may be inserted into a plasmid vector adapted for expression in a bacterial cell, such as E. coli, or a mammalian cell such as CHO or HeLa cells. Alternatively, tagged fusion proteins comprising the variant can be generated. Such variant-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as E. coli or a eukaryotic cell, such as, but not limited to, yeast and mammalian cells (e.g., T cells, hematopoietic cells, etc.). Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

Variant proteins, produced by gene expression in a recombinant prokaryotic or eukaryotic system may be purified according to methods known in the art. In a particular embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

Variant proteins, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems, such as in reticulocyte lysates.

Uses of Variant Proteins and Variant-Encoding Nucleic Acids

Variant nucleic acids encoding polypeptides having altered protease activities may be used according to this invention, for example, as therapeutic and/or prophylactic agents (protein or nucleic acid) which modulate the blood coagulation cascade. In a particular embodiment of the present invention, variant polypeptides may be administered to a patient via infusion in a biologically compatible carrier, e.g., via intravascular or intravenous injection. The variants of the invention may optionally be encapsulated into liposomes or mixed with other phospholipids or micelles to increase stability of the molecule. Variants may be administered alone or in combination with other agents known to modulate hemostasis (e.g., Factor VIII, Factor VIIIa or derivatives thereof). An appropriate composition in which to deliver variant polypeptides may be determined by a medical practitioner upon consideration of a variety of physiological variables, including, but not limited to, the patient's condition and hemodynamic state. A variety of compositions well suited for different applications and routes of administration are well known in the art and are described herein.

The preparation containing the purified variants contains a physiologically acceptable matrix and is preferably formulated as a pharmaceutical preparation. The preparation can be formulated using methods known in the art. In a particular embodiment, the variants can be mixed with a buffer containing salts, such as NaCl or $CaCl_2$, and/or amino acids, such as glycine and/or lysine, and in a pH range from 6 to 8. Until needed, the purified preparation containing the variant can be stored in the form of a finished solution or in lyophilized or deep-frozen form. In a particular embodiment, the preparation is stored in lyophilized form and is dissolved into a visually clear solution using an appropriate reconstitution solution. Alternatively, the preparation according to the present invention can also be made available as a liquid preparation or as a liquid that is deep-frozen.

The preparation according to the present invention which contains a Factor IX variant may further be in combination with Factor VIIa/TF complex or FXIa or a derivative thereof which is able to activate the Factor IX variant into FIXa. In a particular embodiment, the FIXa variant can be made available in the form of a combination preparation comprising a container that holds Factor VIIa/TF complex or FXIa which is immobilized on a matrix, potentially in the form of a miniature column or a syringe complemented with a protease, and a container containing the pharmaceutical preparation with the Factor IX variant. To activate the Factor IX variant, the Factor IX variant-containing solution, for example, can be pressed over the immobilized protease. During storage of the preparation, the Factor IX variant-containing solution is preferably spatially separated from the protease. The preparation according to the present invention can be stored in the same container as the protease, but the components are spatially separated by an impermeable partition which can be easily removed before administration of the preparation. The solutions can also be stored in separate containers and be brought into contact with each other only shortly prior to administration.

The Factor IX variant may be administered to the subject. Alternatively, the Factor IX variant can be activated into FIXa shortly before immediate use, i.e., prior to the administration to the subject. The activation can be carried out by bringing a Factor IX variant into contact with an immobilized protease or by mixing solutions containing a protease, on the one hand, and the Factor IX variant, on the other hand. Thus, it is possible to separately maintain the two components in solution and to mix them by means of a suitable infusion device in which the components come into contact with each other as they pass through the device and thereby to cause an activation into FIXa or into the FIXa variant. The patient thus receives a mixture of FIXa and, in addition, a serine protease which is responsible for the activation. In this context, it is important to pay close attention to the dosage since the additional administration of a serine protease also activates endogenous Factor IX, which may shorten the coagulation time.

The preparation according to the present invention can be made available as a pharmaceutical preparation with FIX activity in the form of a one-component preparation or in combination with other factors in the form of a multi-component preparation.

Prior to processing the purified protein into a pharmaceutical preparation, the purified protein may be subjected to the conventional quality controls and fashioned into a therapeutic form of presentation. In particular, during the recombinant manufacture, the purified preparation may be tested for the absence of cellular nucleic acids as well as nucleic acids that are derived from the expression vector.

Another feature of this invention relates to making available a preparation which contains a FIXa variant with a high stability and structural integrity and which, in particular, is free from inactive Factor IX/IXa intermediates and autoproteolytic degradation products and which can be produced by activating a Factor IX variant of the type described above and by formulating it into an appropriate preparation.

The pharmaceutical preparation of the instant invention may contain, as an example, dosages of between about 1-1000 µg/kg, about 10-500 µg/kg, about 10-250 µg/kg, or about 10-100 µg/kg. The amounts may be administered intravenously at least one a day. Patients may be treated immediately upon presentation at the clinic with a bleed or prior to the delivery of cut/wound causing a bleed. Alternatively, patients may receive a bolus infusion every one to three hours, or if sufficient improvement is observed, a once daily infusion of the variant described herein.

Variant-encoding nucleic acids may be used for a variety of purposes in accordance with the present invention. In a particular embodiment of the invention, a nucleic acid delivery vehicle (i.e., an expression vector) for modulating blood coagulation is provided wherein the expression vector comprises a nucleic acid sequence coding for a variant polypeptide, or a functional fragment thereof as described herein. Administration of variant-encoding expression vectors to a patient results in the expression of variant polypeptide which serves to alter the coagulation cascade. In accordance with the present invention, a variant encoding nucleic acid sequence may encode a variant Factor IX polypeptide as described herein whose expression increases hemostasis. In a particular embodiment, the nucleic acid sequence encodes a human Factor IX or Factor IXa polypeptide variant. Nucleic acid molecules encoding the variants of the instant invention or cells comprising the nucleic acid molecules encoding the variants of the instant invention may be administered to a subject for modulating hemostasis. The nucleic acid molecules may, for example, be expressed in or delivered in platelets, T cells, and/or other hematopoietic cells.

Expression vectors comprising variant nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible composition.

In a particular embodiment of the invention, the expression vector comprising nucleic acid sequences encoding the variant is a viral vector. Viral vectors, with or without tissue specific promoters/enhancers, which may be used in the present invention include, but are not limited to: adenoassociated virus (AAV) vectors (e.g., AAV1, AAV2, AAV3, AAV4, AAV5, AAV6, AAV7, AAV8, AAV9, AAV10, AAV11, AAV12, AAVrh10, or other derivatives and/or alternate serotypes) and hybrid AAV vectors (e.g., a combinatorial hybrid of 2, 3, 4, 5, or more serotypes), lentivirus vectors and pseudo-typed lentivirus vectors (e.g., Ebola virus, vesicular stomatitis virus (VSV), and feline immunodeficiency virus (FIV)), herpes simplex virus vectors, vaccinia virus vectors, and retroviral vectors. The AAV may be a hybrid AAV vector having a capsid protein (e.g., any one or more of AAV serotypes 1-12 and others) and genome (e.g., AAV serotype 2) from different AAV.

In a particular embodiment of the present invention, methods are provided for the administration of a viral vector comprising nucleic acid sequences encoding a variant or a functional fragment thereof. As described herein, expression of a variant polypeptide following administration of such an adenoviral vector serves to modulate hemostasis, particularly to enhance the procoagulation activity.

Also included in the present invention is a method for modulating hemostasis comprising providing cells (e.g., platelets, T cells, hematopoietic cells, etc.) of an individual with a nucleic acid delivery vehicle encoding a variant polypeptide and allowing the cells to grow under conditions wherein the variant polypeptide is expressed. The cells may be administered to the subject.

From the foregoing discussion, it can be seen that variant polypeptides, and variant polypeptide expressing nucleic acid vectors may be used in the treatment of disorders associated with aberrant blood coagulation.

The expression vectors of the present invention may be incorporated into pharmaceutical compositions that may be delivered to a subject, so as to allow production of a biologically active protein (e.g., a variant polypeptide or functional fragment or derivative thereof). In a particular embodiment of the present invention, pharmaceutical compositions comprising sufficient genetic material to enable a recipient to produce a therapeutically effective amount of a variant polypeptide can influence hemostasis in the subject. Alternatively, as discussed above, an effective amount of the variant polypeptide may be directly infused into a patient in need thereof. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents (e.g., co-factors) which influence hemostasis.

In particular embodiments, the pharmaceutical compositions also contain a pharmaceutically acceptable excipient/carrier, as described herein. Such carriers include any pharmaceutical agent that does not itself induce an immune response harmful to the individual receiving the composition, and which may be administered without undue toxicity. Pharmaceutically acceptable carriers include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington: The Science and Practice of Pharmacy (22nd Ed. (2012) Pharmaceutical Press).

Pharmaceutical formulations suitable for parenteral or intravascular administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes.

Optionally, the suspension may also contain suitable stabilizers or agents which increase the solubility of the compounds to allow for the preparation of highly concentrated solutions.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they may be placed in an appropriate container and labeled for treatment. For administration of variant-containing vectors or polypeptides, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques and guidance provided in the present invention. Therapeutic doses will depend on, among other factors, the age and general condition of the subject, the severity of the aberrant blood coagulation phenotype, and the strength of the control sequences regulating the expression levels of the variant polypeptide. Thus, a therapeutically effective amount in humans will fall in a relatively broad range that may be determined by a medical practitioner based on the response of an individual patient to vector-based variant treatment.

The variant polypeptides, alone or in combination with other agents may be directly infused into a patient in an appropriate biological carrier as described hereinabove. Expression vectors of the present invention comprising nucleic acid sequences encoding variant or functional fragments thereof, may be administered to a patient by a variety of means (see below) to achieve and maintain a prophylactically and/or therapeutically effective level of the variant polypeptide. One of skill in the art could readily determine specific protocols for using the variant encoding expression vectors of the present invention for the therapeutic treatment of a particular patient.

Variant encoding adenoviral vectors of the present invention may be administered to a patient by any means known. Direct delivery of the pharmaceutical compositions in vivo may generally be accomplished via injection using a conventional syringe, although other delivery methods such as convection-enhanced delivery are envisioned. In this regard, the compositions may be delivered subcutaneously, epidermally, intradermally, intrathecally, intraorbitally, intramucosally, intraperitoneally, intravascularly, intravenously, intraarterially, orally, intrahepatically, intraosseal, or intramuscularly. Other modes of administration include oral and pulmonary administration, suppositories, and transdermal applications. A clinician specializing in the treatment of patients with blood coagulation disorders may determine the optimal route for administration of the adenoviral vectors comprising variant nucleic acid sequences based on a number of criteria, including, but not limited to: the condition of the patient and the purpose of the treatment (e.g., enhanced or reduced blood coagulation).

The present invention also encompasses AAV vectors comprising a nucleic acid sequence encoding a variant polypeptide. Also encompassed are lentiviruses or pseudotyped lentivirus vectors comprising a nucleic acid sequence encoding a variant polypeptide. Also encompassed are naked plasmid or expression vectors comprising a nucleic acid sequence encoding a variant polypeptide.

The following examples are provided to illustrate various embodiments of the present invention. The examples are illustrative and are not intended to limit the invention in any way.

EXAMPLE 1

A series of recombinant Factor IX derivatives, wherein an amino acid at position 223, 406, or 410 was modified, was tested for activity. Specifically, $Glu^{410}$ was substituted with Lys, Tyr, Arg, or His; $Val^{223}$ was substituted with Tyr; and $Asn^{406}$ was substituted with Arg, Lys, or Gln. Additionally, a Factor IX variant wherein $Glu^{410}$ was substituted with Lys and $Arg^{338}$ was substituted with Leu was generated. Briefly, HEK 293 cells in 100 mm plates were transiently transfected with plasmids expressing the Factor IX variant. Media from the transfected cells was collected at 48 hours and Factor IX activity was assessed in a one stage Factor IX specific clotting assay. Antigen levels were determined with a Factor IX specific ELISA. Factor IX variant specific activity was normalized to antigen levels to control for experimental variation. As shown in Table 1, the above identified substitutions yielded greater specific activity than wild-type Factor IX. Notably, the double mutant enhanced Factor IX specific activity more than 15 fold.

TABLE 1

Activity levels normalized to wild-type FIX activity levels.

| Human FIX | Specific Activity (Fold Increase) |
|---|---|
| Wild-type | 1 |
| E410K | 6.07 |
| E410Y | 5.76 |
| E410R | 4.60 |
| E410H | 3.58 |
| V223Y | 4.05 |
| N406R | 2.73 |
| N406K | 1.92 |
| N406Q | 1.67 |
| E410K R338L | 17 |

Figure 2:
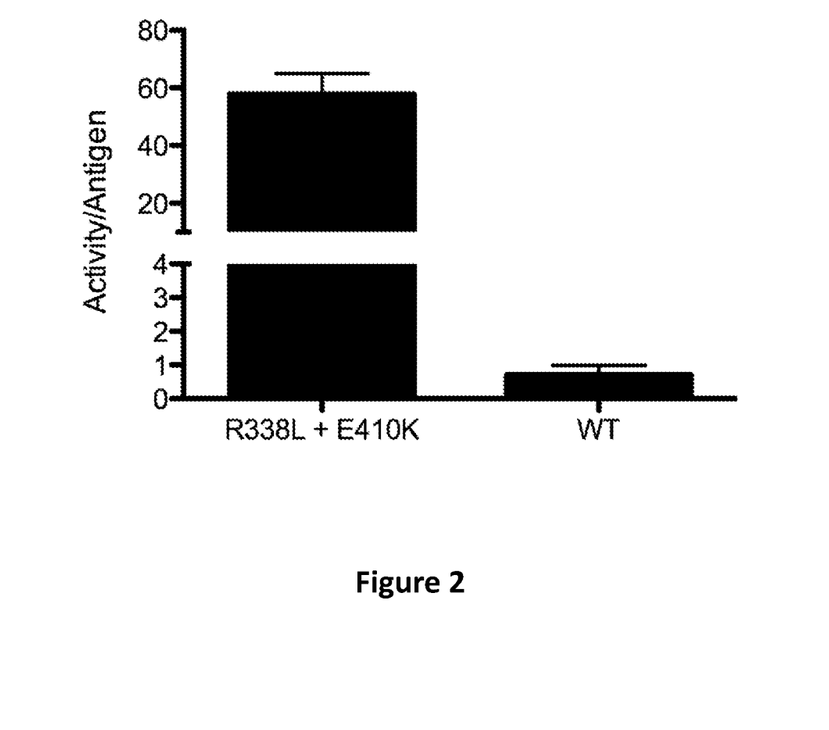
FIG. 2 provides a graph of the specific activity of FIX in hemophilia mice after administration of an AAV8 vector encoding FIX R338L+E410K (n=7) or wild-type FIX (n=2). Values are shown as mean ±SEM.

Hemophilia B mice were intravascularly administered $4 \times 10^{11}$ vector genomes (vg)/kg of AAV8 vectors encoding FIX R338L+E410K (n=7) or WT FIX (n=2) under the control of a liver-specific promoter. FIG. 2 shows in vivo specific activity of the FIX variant (R338L+E410K) and FIX-WT in hemophilia B mice. Plasma samples were collected 4 weeks after vector injection and activity was measured by aPTT-based assay and antigen was measured by FIX ELISA. Significantly, the FIX variant exhibits dramatically greater activity in vivo than wild-type FIX.

EXAMPLE 2

In order to identify novel FIX variants, amino acid positions were selected that: (1) were not reported to be associated with hemophilia B; (2) were highly conserved among species; and (3) were located in regions relevant for protein function. For example, regions which affect the ability of activated FIX to bind activated factor VIII (FVIIIa) or interact with other enzymes participating in the activation of intrinsic pathway. A series of recombinant Factor IX derivatives, wherein an amino acid at position 342 or 343 was modified, was tested for activity. Specifically, $Thr^{343}$ was substituted with Met, Lys, Arg, Gln, or Gly and $Phe^{342}$ was substituted with His.

Briefly, confluent HEK293 cells in 6 well plates are transfected with 10 μg plasmid DNA of each FIX variant using Lipofectamine® 2000 (Invitrogen) according to manufacturer's instructions. Four to six hours after transfection, cells were checked for continued confluence and switched to FIX expression media that includes 10 μg/ml of vitamin K. After 24 hours, conditioned media was collected. The FIX antigen level was determined by a commercial FIX-specific ELISA (Affinity Biologicals, Inc.; Ancaster, ON, Canada) and activity was determined by a aPTT-based clotting assay. Both assays use commercial recombinant FIX (BeneFIX®) as a standard. All experiments were done in triplicate and compared to FIX-WT transfected at the same time (Arruda et al., Blood (2001) 97: 130).

As shown in Table 2, the above identified substitutions yielded greater specific activity than wild-type Factor IX.

TABLE 2

Activity levels normalized to wild-type FIX activity levels.

| Human FIX | | Specific Activity (fold increase) |
|---|---|---|
| Wild-type | | 1 |
| Variants | Amino Acid | |
| T343 | M | 3.69 |
| | K | 3.29 |
| | R | 2.66 |
| | Q | 2.06 |
| | G | 1.65 |
| F342 | H | 3.49 |

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A Factor IX variant, wherein said Factor IX variant comprises a light and heavy chain, wherein the light chain comprises SEQ ID NO: 2, wherein the heavy chain comprises SEQ ID NO: 3, and wherein the Asn at position 261 of SEQ ID NO: 3 is substituted with Arg, Lys, or Gln and, optionally, the Arg at position 193 of SEQ ID NO: 3 is substituted with an amino acid other than Arg.

2. The Factor IX variant of claim 1, wherein the Asn at position 261 of SEQ ID NO: 3 is substituted with Arg.

3. The Factor IX variant of claim 1, wherein the Arg at position 193 of SEQ ID NO: 3 is substituted with Leu.

4. The Factor IX variant of claim 1, wherein the Arg at position 193 of SEQ ID NO: 3 is substituted with an amino acid selected from the group consisting of Gly, Ala, Leu, Val, Ile, and Met.

5. A composition comprising at least one Factor IX variant of claim 1 and at least one pharmaceutically acceptable carrier.

6. An activated Factor IX variant of a Factor IX variant of claim 1.

7. A method for treatment of a hemostasis related disorder in a patient in need thereof comprising administering to the patient a therapeutically effective amount of the Factor IX variant of claim 1 in a pharmaceutically acceptable carrier.

8. The method of claim 7, wherein said hemostasis related disorder is hemophilia B or hemophilia B associated with inhibitory antibodies.

9. The method of claim 7, wherein said coagulation factor deficiency is hemophilia B.

* * * * *

SEQUENCE LISTING

```
<160> NUMBER OF SEQ ID NOS: 8

<210> SEQ ID NO 1
<211> LENGTH: 461
<212> TYPE: PRT
<213> ORGANISM: Homo sapiens

<400> SEQUENCE: 1

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
```

```
                225                 230                 235                 240
        Gln Val Val Leu Asn Gly Lys Val Asp Ala Phe Cys Gly Gly Ser Ile
                        245                 250                 255

Val Asn Glu Lys Trp Ile Val Thr Ala Ala His Cys Val Glu Thr Gly
                        260                 265                 270

Val Lys Ile Thr Val Val Ala Gly Glu His Asn Ile Glu Thr Glu
                        275                 280                 285

His Thr Glu Gln Lys Arg Asn Val Ile Arg Ile Pro His His Asn
            290                 295                 300

Tyr Asn Ala Ala Ile Asn Lys Tyr Asn His Asp Ile Ala Leu Leu Glu
        305                 310                 315                 320

Leu Asp Glu Pro Leu Val Leu Asn Ser Tyr Val Thr Pro Ile Cys Ile
                        325                 330                 335

Ala Asp Lys Glu Tyr Thr Asn Ile Phe Leu Lys Phe Gly Ser Gly Tyr
                        340                 345                 350

Val Ser Gly Trp Gly Arg Val Phe His Lys Gly Arg Ser Ala Leu Val
                        355                 360                 365

Leu Gln Tyr Leu Arg Val Pro Leu Val Asp Arg Ala Thr Cys Leu Arg
            370                 375                 380

Ser Thr Lys Phe Thr Ile Tyr Asn Asn Met Phe Cys Ala Gly Phe His
        385                 390                 395                 400

Glu Gly Gly Arg Asp Ser Cys Gln Gly Asp Ser Gly Gly Pro His Val
                        405                 410                 415

Thr Glu Val Glu Gly Thr Ser Phe Leu Thr Gly Ile Ile Ser Trp Gly
                        420                 425                 430

Glu Glu Cys Ala Met Lys Gly Lys Tyr Gly Ile Tyr Thr Lys Val Ser
                        435                 440                 445

Arg Tyr Val Asn Trp Ile Lys Glu Lys Thr Lys Leu Thr
                        450                 455                 460

<210> SEQ ID NO 2
<211> LENGTH: 145
<212> TYPE: PRT
<213> ORGANISM: Homo sapiens

<400> SEQUENCE: 2

Tyr Asn Ser Gly Lys Leu Glu Glu Phe Val Gln Gly Asn Leu Glu Arg
        1               5                   10                  15

Glu Cys Met Glu Glu Lys Cys Ser Phe Glu Glu Ala Arg Glu Val Phe
                        20                  25                  30

Glu Asn Thr Glu Arg Thr Thr Glu Phe Trp Lys Gln Tyr Val Asp Gly
                        35                  40                  45

Asp Gln Cys Glu Ser Asn Pro Cys Leu Asn Gly Gly Ser Cys Lys Asp
                50                  55                  60

Asp Ile Asn Ser Tyr Glu Cys Trp Cys Pro Phe Gly Phe Glu Gly Lys
        65                  70                  75                  80

Asn Cys Glu Leu Asp Val Thr Cys Asn Ile Lys Asn Gly Arg Cys Glu
                        85                  90                  95

Gln Phe Cys Lys Asn Ser Ala Asp Asn Lys Val Val Cys Ser Cys Thr
                        100                 105                 110

Glu Gly Tyr Arg Leu Ala Glu Asn Gln Lys Ser Cys Glu Pro Ala Val
                        115                 120                 125

Pro Phe Pro Cys Gly Arg Val Ser Val Ser Gln Thr Ser Lys Leu Thr
                        130                 135                 140
```

Arg
145

<210> SEQ ID NO 3
<211> LENGTH: 270
<212> TYPE: PRT
<213> ORGANISM: Homo sapiens

<400> SEQUENCE: 3

Ala Glu Thr Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
            20                  25                  30

Phe Thr Arg Val Val Gly Gly Glu Asp Ala Lys Pro Gly Gln Phe Pro
        35                  40                  45

Trp Gln Val Val Leu Asn Gly Lys Val Asp Ala Phe Cys Gly Gly Ser
    50                  55                  60

Ile Val Asn Glu Lys Trp Ile Val Thr Ala Ala His Cys Val Glu Thr
65                  70                  75                  80

Gly Val Lys Ile Thr Val Val Ala Gly Glu His Asn Ile Glu Glu Thr
                85                  90                  95

Glu His Thr Glu Gln Lys Arg Asn Val Ile Arg Ile Ile Pro His His
            100                 105                 110

Asn Tyr Asn Ala Ala Ile Asn Lys Tyr Asn His Asp Ile Ala Leu Leu
        115                 120                 125

Glu Leu Asp Glu Pro Leu Val Leu Asn Ser Tyr Val Thr Pro Ile Cys
    130                 135                 140

Ile Ala Asp Lys Glu Tyr Thr Asn Ile Phe Leu Lys Phe Gly Ser Gly
145                 150                 155                 160

Tyr Val Ser Gly Trp Gly Arg Val Phe His Lys Gly Arg Ser Ala Leu
                165                 170                 175

Val Leu Gln Tyr Leu Arg Val Pro Leu Val Asp Arg Ala Thr Cys Leu
            180                 185                 190

Arg Ser Thr Lys Phe Thr Ile Tyr Asn Asn Met Phe Cys Ala Gly Phe
        195                 200                 205

His Glu Gly Gly Arg Asp Ser Cys Gln Gly Asp Ser Gly Gly Pro His
    210                 215                 220

Val Thr Glu Val Glu Gly Thr Ser Phe Leu Thr Gly Ile Ile Ser Trp
225                 230                 235                 240

Gly Glu Glu Cys Ala Met Lys Gly Lys Tyr Gly Ile Tyr Thr Lys Val
                245                 250                 255

Ser Arg Tyr Val Asn Trp Ile Lys Glu Lys Thr Lys Leu Thr
            260                 265                 270

<210> SEQ ID NO 4
<211> LENGTH: 235
<212> TYPE: PRT
<213> ORGANISM: Homo sapiens

<400> SEQUENCE: 4

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Thr Gly Val Lys
        35                  40                  45

```
Ile Thr Val Val Ala Gly Glu His Asn Ile Glu Thr Glu His Thr
 50                  55                  60

Glu Gln Lys Arg Asn Val Ile Arg Ile Ile Pro His His Asn Tyr Asn
 65                  70                  75                  80

Ala Ala Ile Asn Lys Tyr Asn His Asp Ile Ala Leu Leu Glu Leu Asp
                 85                  90                  95

Glu Pro Leu Val Leu Asn Ser Tyr Val Thr Pro Ile Cys Ile Ala Asp
             100                 105                 110

Lys Glu Tyr Thr Asn Ile Phe Leu Lys Phe Gly Ser Gly Tyr Val Ser
             115                 120                 125

Gly Trp Gly Arg Val Phe His Lys Gly Arg Ser Ala Leu Val Leu Gln
 130                 135                 140

Tyr Leu Arg Val Pro Leu Val Asp Arg Ala Thr Cys Leu Arg Ser Thr
145                 150                 155                 160

Lys Phe Thr Ile Tyr Asn Asn Met Phe Cys Ala Gly Phe His Glu Gly
                 165                 170                 175

Gly Arg Asp Ser Cys Gln Gly Asp Ser Gly Gly Pro His Val Thr Glu
             180                 185                 190

Val Glu Gly Thr Ser Phe Leu Thr Gly Ile Ile Ser Trp Gly Glu Glu
             195                 200                 205

Cys Ala Met Lys Gly Lys Tyr Gly Ile Tyr Thr Lys Val Ser Arg Tyr
 210                 215                 220

Val Asn Trp Ile Lys Glu Lys Thr Lys Leu Thr
225                 230                 235

<210> SEQ ID NO 5
<211> LENGTH: 1386
<212> TYPE: DNA
<213> ORGANISM: Homo sapiens

<400> SEQUENCE: 5
atgcagcgcg tgaacatgat catggcagaa tcaccaggcc tcatcaccat ctgcctttta    60
ggatatctac tcagtgctga atgtacagtt tttcttgatc atgaaaacgc caacaaaatt   120
ctgaatcggc aaagaggta taattccagt aaattggaag agtttgttca gggaaccctt   180
gagagagaat gtatggaaga aaagtgtagt tttgaagaag cacgagaagt ttttgaaaac   240
actgaaagaa caactgaatt ttggaagcag tatgttgatg agatcagtg tgagtccaat   300 ccatgtttaa atggcggcag ttgcaaggat gacattaatt cctatgaatg ttggtgtccc   360
tttggatttg aaggaaagaa ctgtgaatta gatgtaacat gtaacattaa gaatggcaga   420
tgcgagcagt tttgtaaaaa tagtgctgat aacaaggtgg tttgctcctg tactgaggga   480
tatcgacttg cagaaaacca gaagtcctgt gaaccagcag tgccattcc atgtggaaga   540 gtttctgttt cacaaacttc taagctcacc cgtgctgaga ctgtttttcc tgatgtggac   600
tatgtaaatt ctactgaagc tgaaaccatt ttggataaca tcactcaaag cacccaatca   660
tttaatgact tcactcgggt tgttggtgga gaagatgcca aaccaggtca attcccttgg   720
caggttgttt tgaatggtaa agttgatgca ttctgtggag ctctatcgt taatgaaaaa   780 tggattgtaa ctgctgccca ctgtgttgaa actggtgtta aaattacagt tgtcgcaggt   840
gaacataata ttgaggagac agaacataca gagcaaaagc gaaatgtgat tcgaattatt   900
cctcaccaca actacaatgc agctattaat aagtacaacc atgacattgc ccttctggaa   960
ctggacgaac cctagtgct aaacagctac gttacaccta tttgcattgc tgacaaggaa  1020
tacacgaaca tcttcctcaa atttggatct ggctatgtaa gtggctgggg aagagtcttc  1080
```

```
cacaaaggga gatcagcttt agttcttcag taccttagag ttccacttgt tgaccgagcc    1140
acatgtcttc gatctacaaa gttcaccatc tataacaaca tgttctgtgc tggcttccat    1200
gaaggaggta gagattcatg tcaaggagat agtgggggac cccatgttac tgaagtggaa    1260
gggaccagtt tcttaactgg aattattagc tggggtgaag agtgtgcaat gaaaggcaaa    1320
tatggaatat ataccaaggt atcccggtat gtcaactgga ttaaggaaaa aacaaagctc    1380
acttaa                                                               1386

<210> SEQ ID NO 6
<211> LENGTH: 4
<212> TYPE: PRT
<213> ORGANISM: Artificial Sequence
<220> FEATURE:
<223> OTHER INFORMATION: Amino-terminal sequence of FIXa

<400> SEQUENCE: 6

Val Val Gly Gly
1

<210> SEQ ID NO 7
<211> LENGTH: 4
<212> TYPE: PRT
<213> ORGANISM: Artificial Sequence
<220> FEATURE:
<223> OTHER INFORMATION: Cleavage site
<220> FEATURE:
<221> NAME/KEY: VARIANT
<222> LOCATION: (2)...(2)
<223> OTHER INFORMATION: Xaa is any amino acid
<220> FEATURE:
<221> NAME/KEY: VARIANT
<222> LOCATION: (3)...(3)
<223> OTHER INFORMATION: Xaa is Arg or Lys

<400> SEQUENCE: 7

Arg Xaa Xaa Arg
1

<210> SEQ ID NO 8
<211> LENGTH: 6
<212> TYPE: PRT
<213> ORGANISM: Artificial Sequence
<220> FEATURE:
<223> OTHER INFORMATION: Cleavage site

<400> SEQUENCE: 8

Arg Lys Arg Arg Lys Arg
1               5
```